United States Patent
Albrecht-Laatsch et al.

(10) Patent No.: US 8,771,370 B2
(45) Date of Patent: *Jul. 8, 2014

(54) ORTHOPEDIC DEVICE

(75) Inventors: Erik Albrecht-Laatsch, Rosdorf (DE); Ralf Carstens, Goettingen (DE); Jens Northemann, Duderstadt (DE); Matthias Schilling, Weissenborn-Luderode (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/474,842

(22) Filed: May 18, 2012

(65) Prior Publication Data

US 2012/0277883 A1 Nov. 1, 2012

Related U.S. Application Data

(63) Continuation-in-part of application No. 12/518,329, filed as application No. PCT/IB2007/004480 on Dec. 12, 2007, now Pat. No. 8,202,325.

(30) Foreign Application Priority Data

Dec. 13, 2006 (DE) .......................... 10 2006 059 206

(51) Int. Cl.
*A61F 2/68* (2006.01)

(52) U.S. Cl.
USPC ....................... 623/24; 623/44; 623/50; 322/3

(58) Field of Classification Search
USPC .............. 623/24, 43, 44, 50; 290/53; 322/3, 4
See application file for complete search history.

(56) References Cited

U.S. PATENT DOCUMENTS

| | | |
|---|---|---|
| 5,703,474 A | 12/1997 | Smalser |
| 7,009,350 B1 * | 3/2006 | Gold ............................. 318/142 |
| 7,652,386 B2 * | 1/2010 | Donelan et al. ............... 290/1 R |
| 2006/0249315 A1 | 11/2006 | Herr et al. |

FOREIGN PATENT DOCUMENTS

| | | |
|---|---|---|
| DE | 195 19 789 | 12/1996 |
| EP | 1 010 407 | 6/2000 |
| EP | 1 532 951 | 8/2003 |
| JP | 6 225899 | 8/1994 |
| SU | 1577784 A1 | 7/1990 |
| WO | WO 99/08621 | 2/1999 |
| WO | WO 2006/099580 | 9/2006 |
| WO | WO 2007/025116 | 3/2007 |

OTHER PUBLICATIONS

Shenck, Nathan S., et al., "Energy Scavenging with Shoe-Mounted Piezoelectrics", IEEE, pp. 30-42 (May/Jun. 2001).

* cited by examiner

*Primary Examiner* — Bruce E Snow
(74) *Attorney, Agent, or Firm* — Whitham Curtis Christofferson & Cook, PC

(57) ABSTRACT

An orthopedic device includes two components that are configured to be movable relative to on another (e.g., longitudinally translatable, pivotable, etc.). The relative movement of the two components is transmitted as unidirectional mechanical energy by means of a transmitting mechanism which includes an energy accumulator connected to a generator. The mechanical energy is thereby converted to electric power.

11 Claims, 9 Drawing Sheets

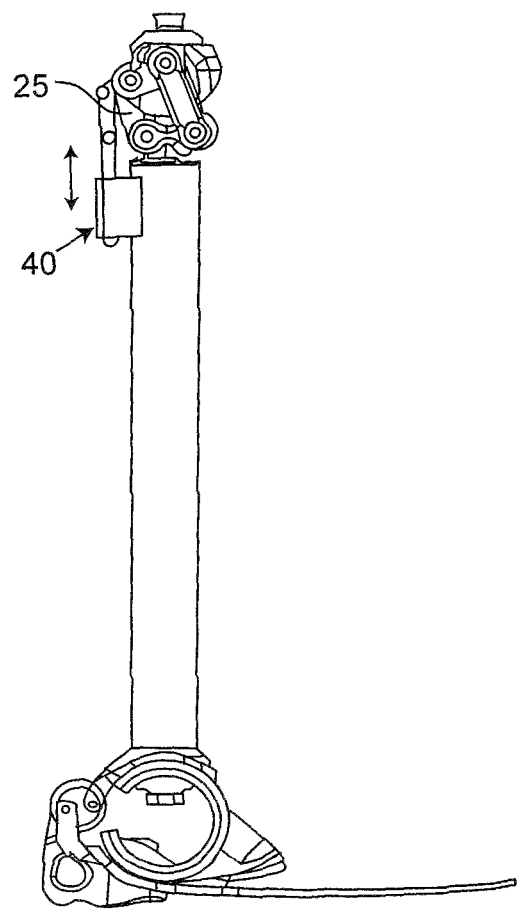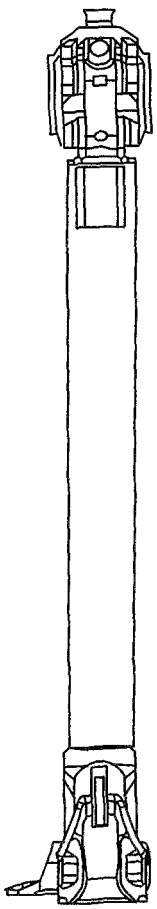
Fig. 2A    Fig. 2B
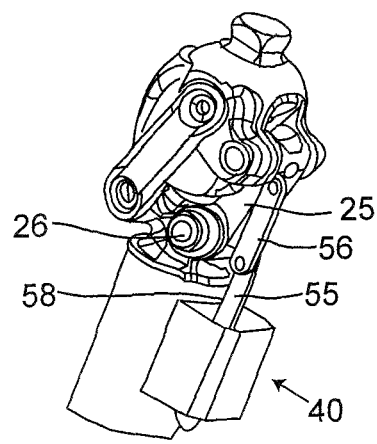
Fig. 2C

ORTHOPEDIC DEVICE

CROSS-REFERENCE TO RELATED APPLICATIONS

This application is a continuation-in-part (CIP) application of U.S. Ser. No. 12/518,329, filed Dec. 14, 2009, now U.S. Pat. No. 8,202,325, which was a filing made under 35 USC 371 for PCT/IB2007/004480 filed Dec. 12, 2007 with a claim of priority to German Patent Application DE 10 2006 059 206.9 filed Dec. 13, 2006, and the complete contents of these prior applications is herein incorporated by reference.

BACKGROUND OF THE INVENTION

1. Field of the Invention

The invention relates to an orthopedic device, especially ortheses or prostheses having components that are mounted so as to be pivotable with respect to one another.

2. Description of Related Art

Orthopedic devices having two components that are articulated and mounted so as to be pivotable with respect to one another are equipped with sensors and actuators for specific applications. Based on the acquired sensor data, changes can be made to the orthopedic device. For example, the damping properties of a joint can be changed as a function of the acquired sensor data. Likewise, it is possible to initiate movement-assisting measures via actuators or equip the orthopedic device just with sensors, whose sensor signals, e.g. can be wirelessly transmitted to a receiver. This makes it possible for the prostheses user in question to monitor or check the device during use so that any adjustments that may need to be made can be done more easily.

Generally, the sensors or actuators or transmission devices are supplied with electrical power from a battery, which ensures uninterrupted operation over a set time period. This period comprises the typical active period during a day, whereas the battery is charged during an inactive period. The batteries that can be used for operation of the orthopedic devices are limited both in their dimensions and in their weight because in orthopedic devices the components that are used need to be as small and lightweight as possible. This results in a limited charging capacity of the battery. Therefore, is problematic to provide additional sensors or actuators or to provide effective assistance of a movement using minimal equipment. The operating times are also limited.

U.S. Pat. No. 5,703,474 describes converting mechanical force to electric power and to thereby charge a battery. Using the ground reaction force produced by the weight of a person while he/she runs to generate piezoelectric energy is also known. In the IEEE-MICRO issue of May-June 2001, pages 30-42, a piezoelectric arrangement is described that is applied to a flexible sheet on a shoe sole. The generated power is used to illuminate the shoe soles. The electrical power that can be generated by using the piezoelectric element on a flexible sheet is minimal and therefore not suitable for use in an orthopedic device.

BRIEF SUMMARY OF THE INVENTION

Am object of the present invention is to improve an orthopedic device having two components that are mounted so as to be movable (e.g., longitudinally displacable, pivotable, etc.) with respect to one another and any sensors or actuators assigned to them in such a way that a sufficient supply of power is ensured and as lightweight a design as possible is achieved.

The orthopedic device according to the invention having two components that are mounted so as to be moveable with respect to one another provides that a generator for generating electric power is arranged on it. The generator is driven via a transmitting mechanism that transmits a relative movement of the two components with respect to each other. In the movement of an orthopedic device, especially during walking, relatively high amounts of energy are provided for brief periods of time in the form of bending moments.

These high amounts of energy are derived from the impulse that occurs in the taking of a step and absorption of the body weight and the leverage ratio at the joint in question. Likewise, in other prosthetic or othotic devices, such as in the upper extremities or in a lumbar orthesis, high bending moments may occur. In order to be able to use these short-term energy infusions, a transmitting mechanism is provided that converts a translatory or rotational movement in such a way that a generator for generating electric power is driven in a preferably rotational manner. This drive is preferably configured in such a way that only one direction of rotation is possible for the generator drive shafts so as to minimize the effort involved in reversing the generator's direction of rotation. Likewise, by using a drive in only one direction of rotation, an energy accumulator, in particular a spring, can be more easily impinged, in particular loaded, and used effectively. The generator is preferably designed as an alternating current generator that is attached to the orthesis or prosthesis and supplies energy to the components that consume energy, such as actuators or sensors. The generator here operates according to the dynamo principle of electromagnetic induction and can alternatively be designed as a direct current generator.

Another way to make the provision of energy more consistent is to connect an energy accumulator in series with the generator. The energy accumulator is preferably designed as a spring, especially a helical or coil spring, and is used to smooth or collect movement impulses. Such springs are sufficiently well known from clock design and ensure that the generator is powered via the gear unit at a correspondingly high rotational speed as long as the pretensioning of the spring is high enough. Because both the gear unit and the generator are kept in motion by the energy accumulator, no cohesive friction effects or startup losses occur, which further increases the efficiency. To increase the efficiency and to make the drive of the generator more consistent, a gear unit is preferably connected in series with the generator and transmits the relatively short length of movement of two components that are pivotable with respect to one another into a rotational speed adapted to the generator.

By this rotation the second freewheel device 138 will be turned and rotation of The spindle 130 is transferred to the spiral spring 270. The spring 270 will be loaded and Rotates the shaft 192 to drive the generator 190 by exerting a torque.

To ensure that the generator or energy accumulator is always driven in a consistent direction of rotation, the transmitting mechanism has at least one freewheel that blocks the transmission of force in a set direction of rotation and permits only a transmission of force in the other, enabled direction of rotation. For alternating movements, such as occur with joint devices within the context of flexion and extension, a drive in one direction of rotation is ensured in this manner.

In one embodiment of the invention, it is provided that the transmitting mechanism has a connecting rod that converts a rotation of two components, such as a foot portion and a lower leg portion or an upper portion and a lower portion of a knee joint device, into a translatory motion. This translatory motion is alternating, where a corresponding control of the connecting rod ensures that a drive of the generator or an impingement of an energy storage device occurs in only one direction. The connecting rod makes it possible to realize a conversion, so that the relatively small rotational angle can be converted into large translatory movements. Likewise, it is possible for the connecting rod to be connected to the generator via a joint mechanism or to the gear unit connected in series with the generator.

In order to ensure an impingement of the generator or the energy accumulator or the gear unit with a displacement force by the connecting rod in only one direction, the connecting rod can be assigned to a ratchet mechanism, which only operates in one direction, but slips through in the other direction. Instead of a conversion via a connecting rod, the transmitting mechanism can transmit the rotational movement directly to the generator or an energy accumulator connected in series or a gear unit connected in series. The transmission of the swiveling of two components can be accomplished via various means, for example, gears or friction wheels or traction mechanisms, such as, chains, belts or toothed belts. Likewise, the various transmitting mechanisms can be combined with each other to realize suitable gear ratios, rotational angles or displacement movements or to guide the forces and moments to the desired positions.

Moreover, it is possible that the transmitting mechanism has a dual gear arrangement with at least one switching device that produces or enables a transmission of force on a driven shaft only in one direction of rotation, so that the gears are active in one direction of force. Here, it is provided that a reversal of direction occurs on a gear, most simply via an interposed gear, to ensure a uniform direction of rotation for the driven shaft and, thus, the generator. A corresponding switching or, for example, a sliding block guide makes it possible for translatory or rotational movements in different directions each to be transmitted to a gear that, via suitable transmission mechanisms, rotates the drive shaft only in one direction of rotation and in the other direction is blocked or not driven at all. Instead of a switching of the gears, they can also be provided with a freewheel and driven simultaneously, where one gear is provided with a device for reversing the direction of rotation so that, when there are alternating movements, drive occurs only in one direction.

An especially simple way of utilizing and transmitting force in only one direction of rotation is present if a bevel gear set is provided in which a bevel drive gear is coupled with two bevel driven gears. The bevel driven gears are mounted on a common driven shaft and each is provided with a freewheel that is designed in such a way that torque is applied to the drive shaft in only one direction of rotation. Because both driven gears are alternately driven with alternating rotational movements, when there is rotation in one direction of rotation, only the one driven gear is coupled to the driven shaft to transmit power, and in the other direction of rotation, the opposite driven gear is coupled to the driven shaft to transmit power.

The generator can be coupled with a battery or with a capacitor in order to provide, in addition to a mechanical storage of energy, also an electrical storage of energy. When an alternating current generator is used, a rectifier needs to be provided to charge a battery. Especially when there is an interposed spring, a constant drive can be controlled via an additional mechanical brake. It is also possible to control the output drive via a short-circuit protection circuit in the generator. Via constant drive of the generator, an essentially steady generation of energy is possible, so that a transformer can be omitted, which has positive effects on both the structural size and the weight.

BRIEF DESCRIPTION OF THE DRAWINGS

Exemplary embodiments of the invention are explained in detail below in reference to the Figures.

FIGS. 2a-2c—show a variant with a translatory transmission;

DETAILED DESCRIPTION

Figures 1A, 1B:
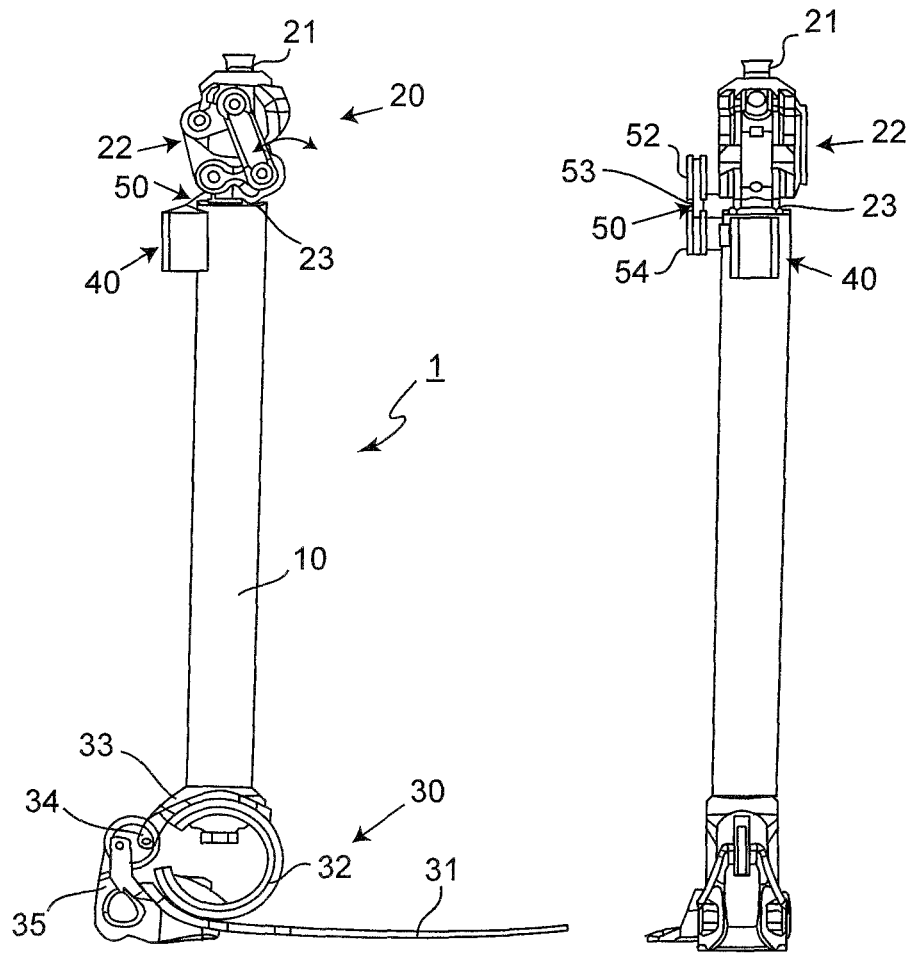
FIGS. 1a-1c—show three views of a first embodiment with direct rotational movement transmission.

FIG. 1 shows an orthopedic device 1 in the form of a leg prosthesis in a side view. A prosthetic knee joint 20 is arranged at the top end of a lower leg shaft 10, and a prosthetic foot 30 is arranged at the bottom end. A sole area 31 is arranged on a joining element 33 via a spring 32. Lower leg shaft 10 is articulated via a joint device 34 on a heel element 35 to which sole portion 31 is also attached.

Prosthetic knee joint 20 is arranged at the top end of lower leg shaft 10 with upper connecting mechanism 21 to hold a thigh shaft or the like. Lower connecting mechanism 23 affixes prosthetic knee joint 20 to lower leg shaft 10. A linkage system 22 provides an articulated connection of the upper connecting mechanism 21 to the lower connecting mechanism 23 or the lower leg shaft 10.

A generator unit 40, which is driven via a transmitting mechanism 50, is attached to lower leg shaft 10. In FIG. 1b, in which orthopedic device 1 is represented in reverse elevation, it can be recognized that transmitting mechanism 50 is arranged to the side of prosthetic knee joint 20 and has two wheels 52, 54, which are connected to each other via a toothed belt 53 or via another traction mechanism. This can be seen in greater detail in FIG. 1c. The prosthetic knee joint 20 has in the linkage system 22 a front swivel arm 24, which is mounted so as to be pivotable with respect to lower connecting mechanism 23 and, thus, with respect to lower leg shaft 10. First drive wheel 52 is attached to front swivel arm 24 or its axis of rotation in a rotationally fixed manner, so that when prosthetic knee joint 20 is bent or extended, a rotation of front swivel arm 24 occurs. The alternating swivel arm movements are indicated by the double arrow in FIG. 1a. If in the course of flexion of prosthetic knee joint 20 front swivel arm 24, starting from the illustrated extended position, swivels in the clockwise direction, drive wheel 52 rotates correspondingly and drives toothed belt 53 or another force transmission element accordingly. A drive wheel 54, which is connected to generator unit 40, is alternately moved correspondingly about its axis of rotation. The rotation of drive wheel 54 is transmitted to a generator, which is explained in detail further below. Where applicable, the kinetic energy can be stored via an energy accumulator in the form of a spring. Likewise, it is possible to interpose a gear mechanism. The rotary movement of front swivel arm 24 is converted via traction mechanism 53 into a direct rotary movement of drive wheel 54 and, thus, of a drive shaft for the generator.

Figure 1C:
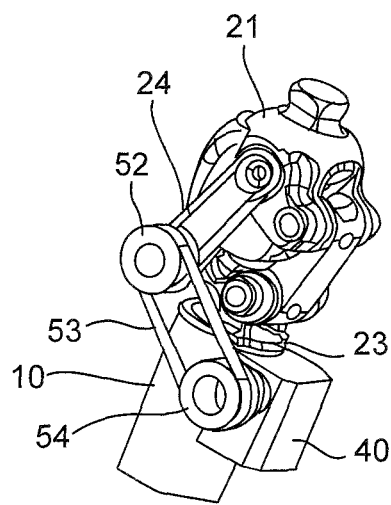

A variant of the invention is depicted in FIGS. 2a to 2c, which are arranged corresponding to FIGS. 1a to 1c. Instead of a transmission of a swiveling of a front swivel arm 24, a relative swiveling of a rear swivel arm 25 about a lower axis of rotation 26 is transmitted via two connecting rods 55, 56 to generator unit 40. Instead of a side-by-side arrangement, as is shown in FIGS. 1a to 1c, knee joint 20 becomes narrower due to the in-line arrangement in the sagittal plane shown in FIGS. 2a to 2c. A set of teeth 58 by which a generator is driven indirectly or directly is configured on connecting rod 55, which engages directly in generator unit 40.

Figure 3A:
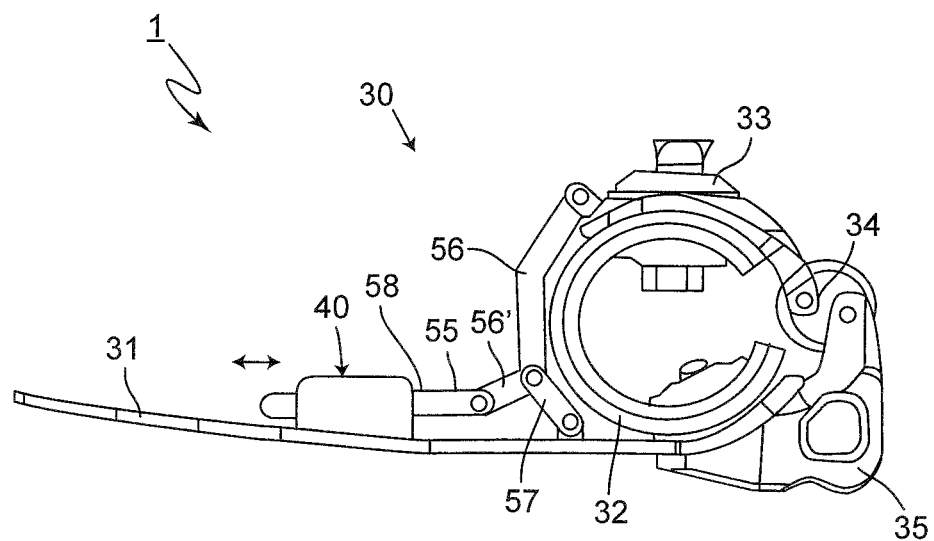
FIGS. 3a and 3b—shown views of an arrangement on a prosthetic foot.
Figure 3B:
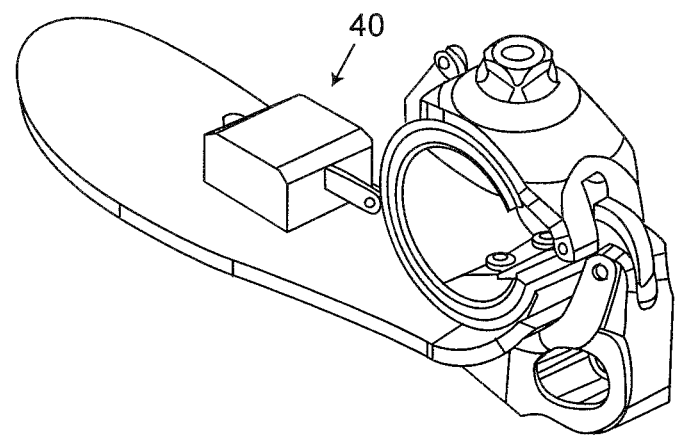

In FIGS. 3a and 3b, a prosthetic foot 30 is shown as orthopedic device 1 in which energy is converted into electric power directly on prosthetic foot 30. Generator unit 40 is arranged on sole portion 31 and via a gear rack 55 with a set of teeth 58 is coupled above a linkage mechanism 56, 56', 57 to pivot-mounted connecting part 33. When there is a load, for example, a load on the front part of the foot via lower leg shaft 10 (not depicted), spring 32 is compressed or rolled in, so that the upper connecting mechanism 33 can swivel about swivel axis 34 in relation to heel portion 35 and sole portion 31. As a result, gear rack 55 is moved forward via linkage mechanism 56, 56', 57. If upper connecting mechanism 33 swings back in the clockwise direction into the depicted original position, gear rack 55 is pulled to the right. The alternating translatory movement of gear rack 55 is indicated by the double arrow. Within generator unit 40, the translatory movement is converted into a rotary movement and a generator (not depicted) is driven.

Figure 4A:
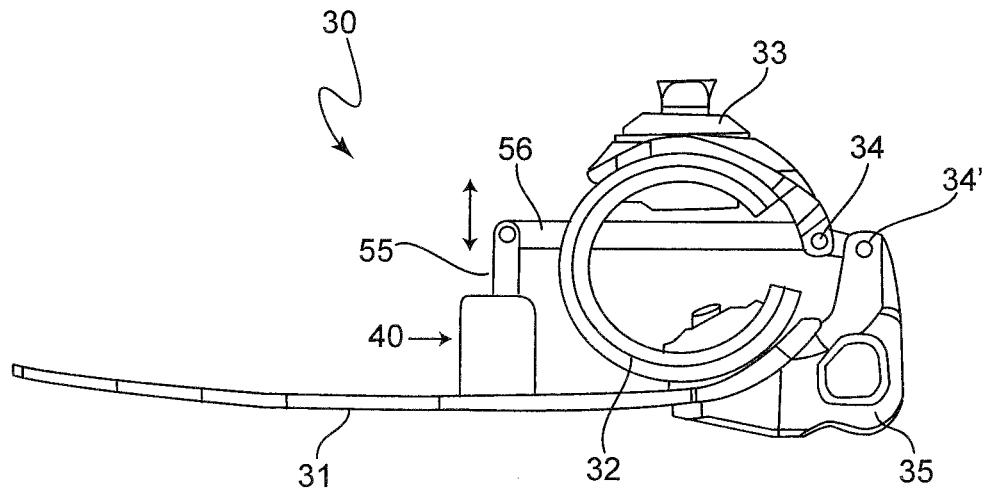
FIGS. 4a and 4b—show a variant of FIG. 3.
Figure 4B:
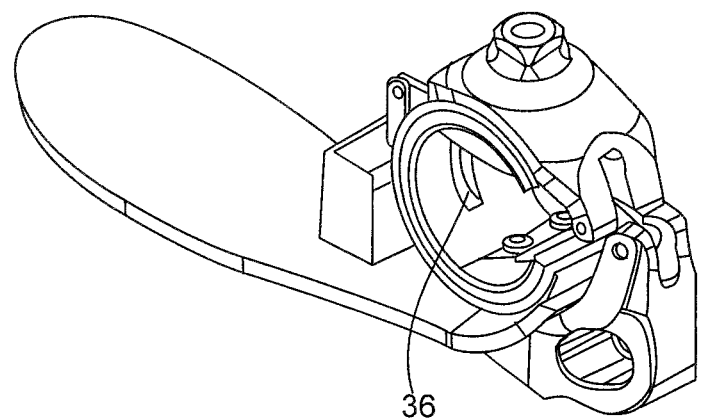

An alternative embodiment of a prosthetic foot 30 is shown in FIGS. 4a and 4b in which upper portion 33 is pivot-mounted about a swivel axis 34 on support beam 56, which in turn is articulated on a vertically oriented gear rack.

Support beam 56 swivels about swivel axis 34' when there is a load and brings about a movement of gear rack 55 in the direction of sole portion 31. If the load is abolished, the depicted original position is restored by spring 32, so that gear rack 55 is shifted upward. This is indicated by the double arrow. Support beam 56 passes through a slot 36 inside spring 32, whereupon a very compact structure can be realized.

Figure 5A:
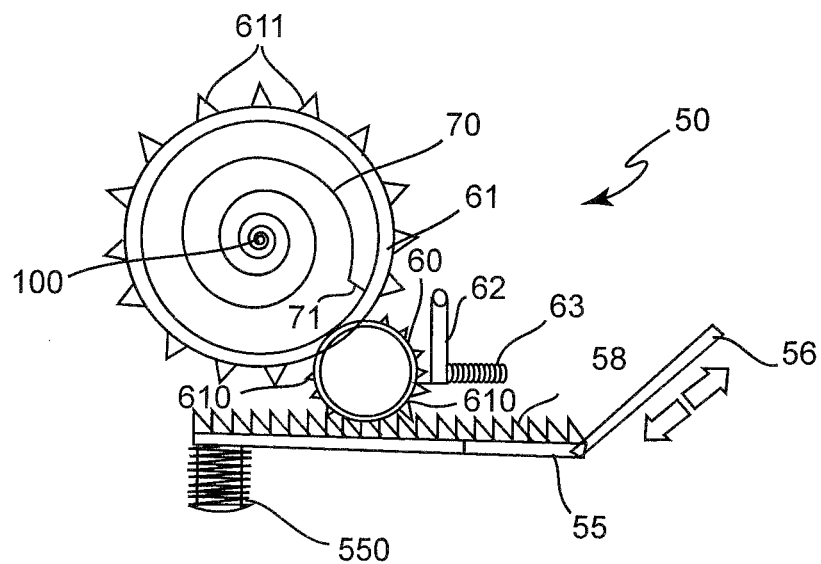
FIGS. 5a-5b—show a schematic diagram of a transmitting mechanism with connecting rod.

FIG. 5 shows a basic diagram of a transmitting mechanism 50 having a connecting rod 56 that executes an alternating, translatory movement. Connecting rod 56 is coupled to a gear rack 55 on which a set of teeth 58 is arranged in a sawtooth configuration. Gear rack 55 meshes with a gear 60, which in turn is engaged with another gear 61. Via this second gear 61, a helical spring 70 is loaded as an energy accumulator. If gear rack 55 is shifted to the left, gear 60 is turned in the clockwise direction, whereupon second gear 61 is turned counterclockwise and loads helical spring 70. When there is a movement to the right, gears 58 slide back over gear 60 without causing a shift. A reset spring 550 then presses gear rack 55 back against gear 60, to keep teeth 58 engaged. For protection, a mechanical brake 62 is pretensioned with a spring 63 against gear 60, so that any counterclockwise movement of gear 60 is blocked. Gears 60, 61 can be coupled to each other in various ratios through an interposed set of gears.

Figure 5B:
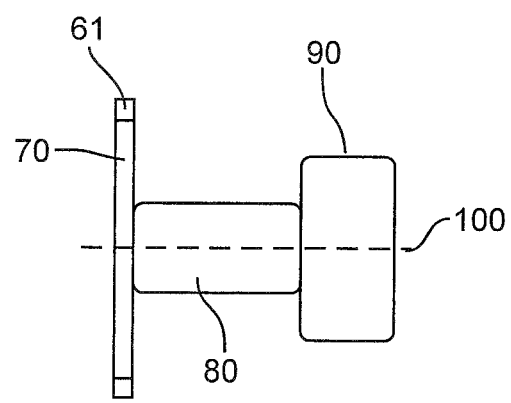

In FIG. 5b, a side view of the relationship of helical spring 70 via gear 61 to a rotating spindle 100 is shown. Torsion spring 70 drives a direct current generator 90 via a transmission 80 having a high gear reduction. As soon as the cohesive friction of the gears is overcome, generator 90 starts to rotate via the sharp gear reduction of transmission 80 and under corresponding pretensioning of spring 70 reaches a high rotational speed, which is maintained as long as the loading of spring 70 is sufficient.

During walking, the short-term infusions of energy achieved and produced in prosthetic foot 30 or in prosthetic knee joint 20 can be stored by spring 70 in the form of repeated rotation of spring 70 into a loaded position and slowly dispensed via gear set 80 to generator 90. This serves to produce a smoothing and a collecting of impulses and to increase the overall efficiency.

Via a movement control, such as via a sliding block guide of gear rack 55, a ratchet configuration of the movement converter in transmitting mechanism 50 can also be omitted. Likewise, alternating rotary movements can be converted via corresponding freewheel arrangements and a reversing mechanism in such a way that a drive shaft for generator 90 or for the pre-tensioning of spring 70 always turns only in one direction.

Figure 6A:
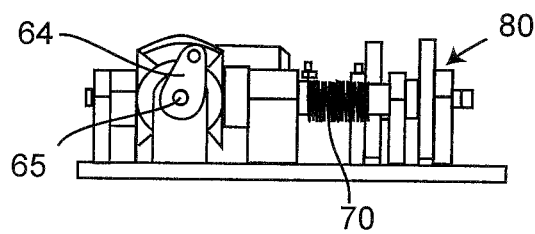
FIGS. 6a-6c—show various views of a variant of the transmitting mechanism.
Figure 6B:
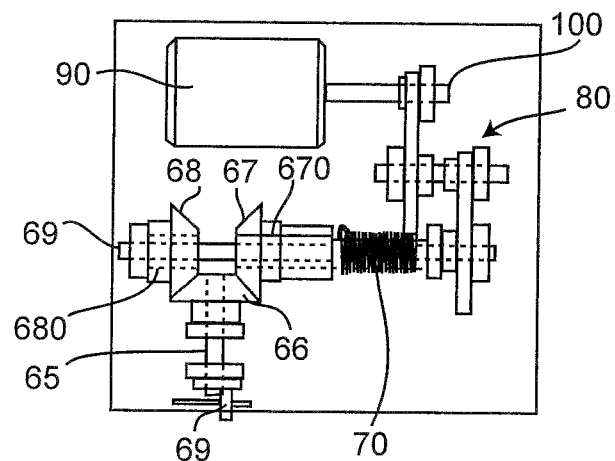
Figure 6C:
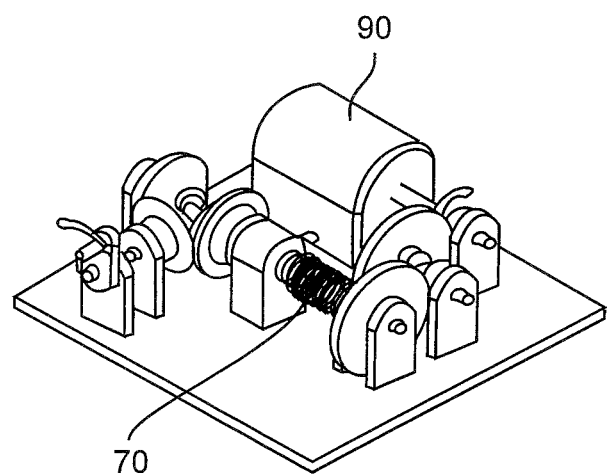

An alternative or supplementary conversion of an alternating translatory movement into a rotary movement is shown in FIGS. 6a to 6c. Via a crank 64, a rotary movement is transformed into an alternating rotary movement on a shaft 65. Mounted on this shaft 65 is a bevel drive gear 66, which carries out alternating rotary movements corresponding to the rotary movement of shaft 65. Two driven gears 67, 68 in the form of bevel gears, each of which is equipped with freewheel mechanisms 670, 680 and is mounted on a common driven shaft 69, engage in drive gear 66. If shaft 65 and drive gear 66 rotate in the clockwise direction, when seen in the viewing direction of 6a, right driven gear 67 remains without any transmission of force, while left driven gear 68 drives driven shaft 69 accordingly. When crank 64 swivels to the left, shaft 65 rotates in the counterclockwise direction, whereupon left gear 68 is disengaged from force transmission via freewheel 680 and in its place right gear 67 is switched to force transmission.

As a result, during both an extension and a flexion of the components of the orthopedic device, driven shaft 69 rotates in only one direction when there is a corresponding transmission of force by transmitting mechanism 50.

Driven shaft 69 is coupled to a helical or coil spring 70 as a mechanical energy accumulator, which in turn is coupled to a gear unit 80. Generator 90 is driven via various gear ratios of gear unit 80, whereupon the kinetic energy stemming from the flexion or extension or, respectively, the relative displacement of the components of the orthopedic device is converted into electric power. This electric power can be conveyed directly to loads, such as actuators or sensors or transmission devices (not depicted). Likewise, it is possible for the generated electric power to be stored in batteries or capacitors.

To enable constant drive, spring 70 can be controlled via a mechanical brake. The drive can also be controlled via a short-circuit protection circuit inside generator 90.

Instead of a translatory movement via a crank 64, drive shaft 65 can also be rotationally driven directly via a toothed belt or the like. In principle, it is also possible for drive shaft 65 or even generator shaft 100, when there is a generator, to be arranged on an axis of rotation of the mounted components.

Figure 7:
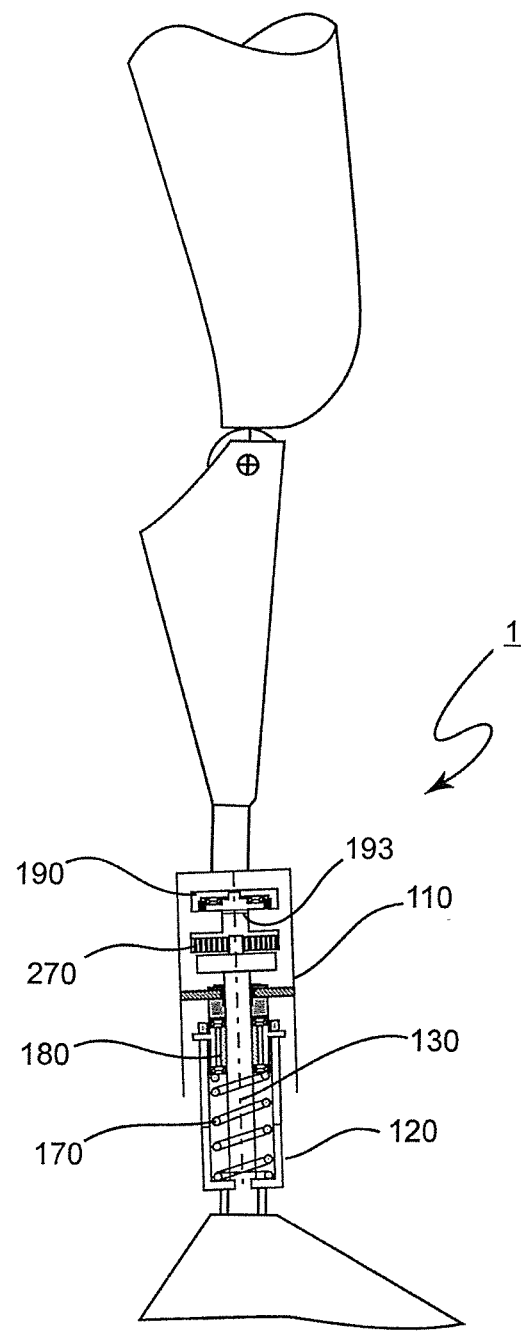
FIG. 7—shows an orthopedic device according to another embodiment of the invention.

FIG. 7 shows an orthopedic device, more specifically a prosthetic leg with a socket, a prosthetic knee joint, a lower leg part and a prosthetic foot. The lower leg part is divided in an upper part 110 and a lower part 120. The upper part 110, which is rigidly connected to the distal part of the knee joint, establishes a kind of housing in which a generator 190 for the generation of electric power is arranged. In front of the generator 190 an energy accumulator or energy storing device in form of a spiral spring 270 is arranged.

The spiral spring 270 is driven by a spindle 130, more specific a ball screw or ball spindle, which is rotatably supported but axially fixed in the lower part 120. The upper part 110, together with the generator, the spiral spring and other devices, is supported by a helical spring 170, which can be compressed during the heel strike and the stance phase. The spring 170 expands after lifting the prosthetic foot.

Figure 8:
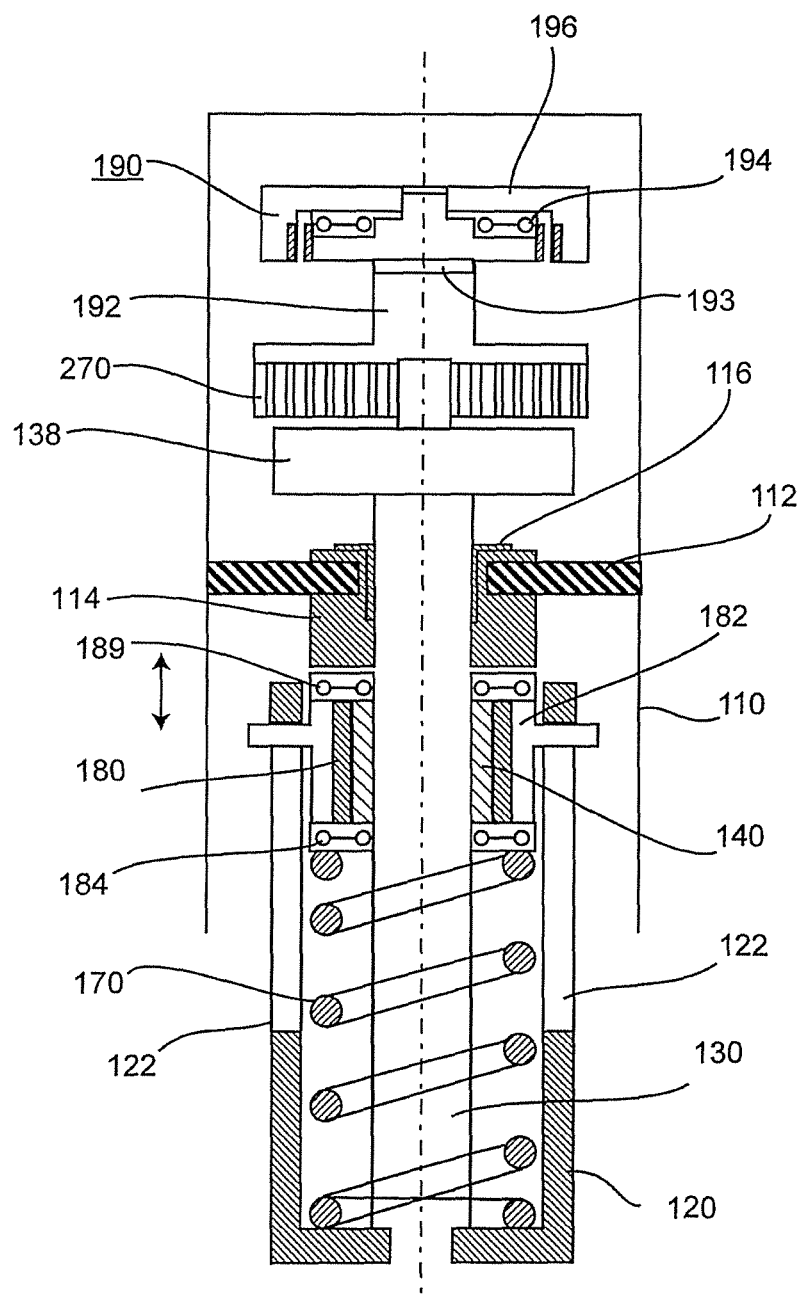
FIG. 8—shows an enlarged view of components depicted in FIG. 7.

FIG. 8 shows an enlarged view of the essential parts of the device, namely the upper part 110 and the lower part 120. The lower part 120 is preferably established as a housing in form of a cylinder in which the ball screw or ball spindle 130 is supported so that it can rotate around its longitudinal axis. The helical spring 170 is arranged around the spindle 130 inside the housing of the lower part 120. Inside the housing of the lower part 120 two slots 122 are provided for receiving projections 182 of a freewheel device 180. By the slots 122 and the projections 182 it is possible to keep the freewheel device 180 together with the freewheel receiving device with the projections 182 longitudinally displaceable relative to the housing 120 as well as unrotatable about the longitudinal axis of the ball spindle 130. Inside of the freewheel device 180 a spindle nut 140 is arranged. The spindle nut 140 is fixed to the free-wheel 180 so that both parts are longitudinally displaceable along the longitudinal axis of the ball screw and rotatable in one direction, whereas the rotation in the opposite direction is blocked by the freewheel device 180. The freewheel device 180 together with the spindle nut 140 and the rotation prevention device in form of projections 182 are supported by two axial bearings 184 positioned at the proximal and distal end of the spindle nut 140.

In the upper part 110 a supporting disk 112 is positioned for receiving guides 114, 116 for supporting and guiding the spindle 130. The guides 114, 116 as well as the supporting disk 112 are fixed inside the upper part 110. At the upper end of the spindle 130 a second free-wheel device 138 can be arranged to drive the spiral spring 270 in only one direction. The second freewheel device 138 is not mandatory.

The spiral spring 270 drives a shaft 192 on which the generator 190 is arranged. One part of the generator 190, which is arranged on the shaft 192, rotates relatively to the fixed part 196 of the generator, so that electrical energy can be produced by the relative movement of the parts 192, 196 to each other.

A further development of the invention provides that a blocking device 193 is assigned to the generator and blocks the drive of the generator if the power level of the energy accumulator is too low. This ensures that in the case of a spring energy accumulator, for example, the generator is not placed in operation until a minimum stress of the spring is reached. This can be done by mechanically blocking the generator, the energy accumulator or an intermediately connected gear unit, or via an electric blocking circuit that blocks them, such as a short-circuit protective circuit.

The device works as follows. When putting weight onto the device 1, the upper part 110 is pressed against the lower part 120. The helical spring 170 will be compressed. Due to the freewheel device 180 the spindle 130 will not be driven but kept in place without rotating about its longitudinal axis. By compressing the helical spring 170 the energy is accumulated or stored. As soon as the weight is taken away from the prosthetic foot the helical spring 170 expands and presses the upper part 110 away from the lower part 120. During this movement the spindle 130 is rotated. In other words, by pushing down the upper part 110 no rotation but compression of the spring takes place, by moving apart the parts, the spindle 130 is driven because of locking of the freewheel device 180 in that direction. The principle is similar to the principle of a humming top.

By this rotation the second freewheel device 130 will be turned and the rotation of the spindle 130 is transferred to the spiral spring 270. The spring 270 will be loaded and rotates the shaft 192 to drive the generator 190 by exerting a torque.

The spiral spring 270 has the effect that the generator 190 is driven constantly in only one direction. The freewheel device 138 prevent the return of energy of the spiral spring 290 to the spindle 130.

Figure 9:
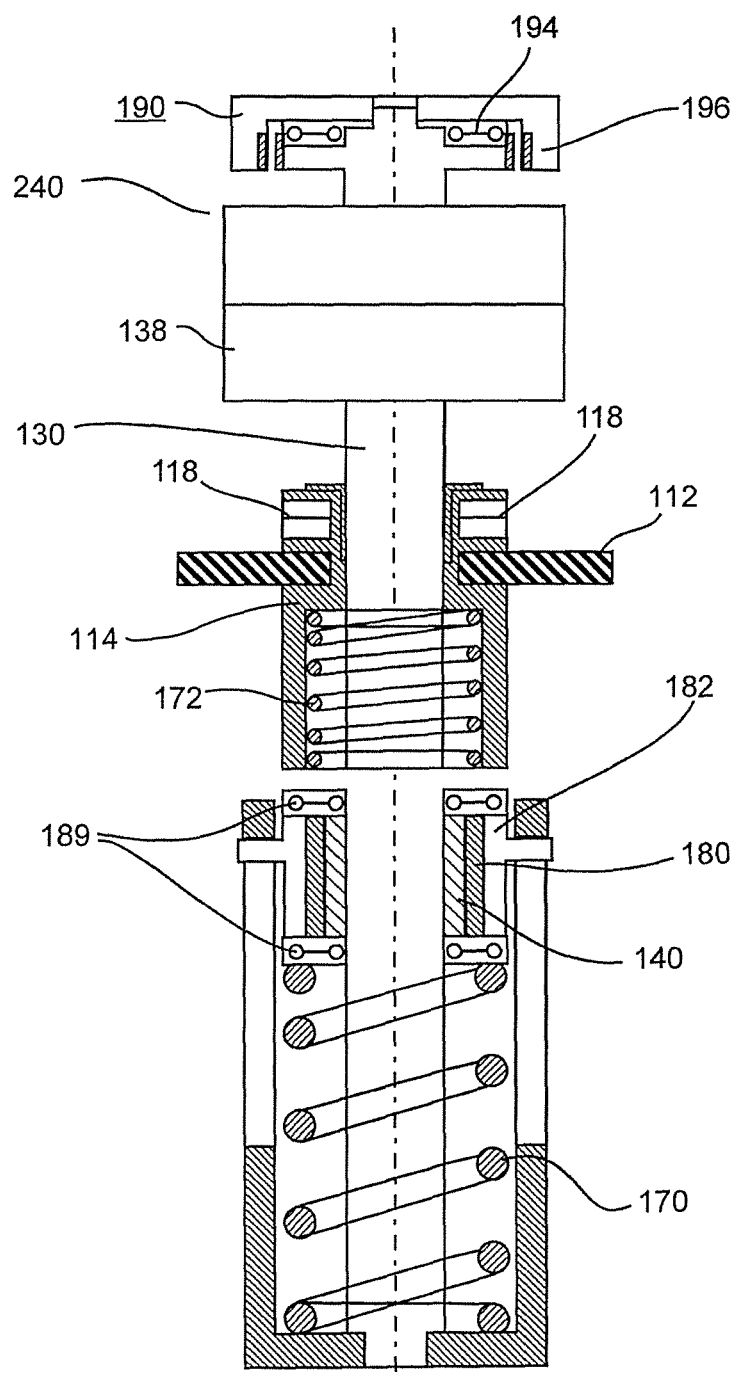
FIG. 9—shows an alternative embodiment of the transmitting device shown in FIG. 8.

FIG. 9 shows a second embodiment of the transmitting device with an additional spring 172 acting on the proximal axial bearing 184 to bias the freewheel device 180 and the spindle nut 140 to avoid rattling during the use of the device. In the guide 114 seatings 118 are provided for receiving the supporting disk 112.

The invention claimed is:

1. An orthopedic device comprising:
   i) two components that are movable with respect to one another;
   ii) a transmitting mechanism for transmission of a force in response to a longitudinal displacement of said two components with respect to each other;
   iii) a mechanical energy accumulator which receives said force from said transmitting mechanism and accumulates a mechanical energy, wherein said transmitting mechanism and said mechanical energy accumulator are configured to allow transmission of said force from said transmitting mechanism to said mechanical energy accumulator only in one direction, wherein the mechanical energy accumulator is a spring; and
   iv) a generator connected to said mechanical energy accumulator for the generation of electric power from said mechanical energy when said mechanical energy is provided to said generator,
   wherein the transmitting mechanism has dual gears which produce a transmission of force on a drive shaft only in one direction,
   wherein the orthopedic device is a prosthesis or orthesis, and
   wherein said generator generates a sufficient supply of power to a component which consumes energy which is associated with said prosthesis or orthesis.

2. The orthopedic device of claim 1, wherein the generator is a direct current or alternating current generator.

3. The orthopedic device of claim 1, wherein a gear set is connected in series with the generator.

4. The orthopedic device of claim 1, wherein a blocking device is provided for the generator, wherein the blocking device blocks electrical power generation until the mechanical energy accumulator has reached a minimum power level.

5. The orthopedic device of claim 1, wherein the transmitting mechanism has at least one freewheel that blocks one direction of force transmission.

6. The orthopedic device of claim 1, wherein the transmitting mechanism has a connecting rod that transmits a relative rotary movement of the two components with respect to each other into a translatory movement.

7. The orthopedic device of claim 6, wherein the connecting rod is coupled to the generator via a ratchet mechanism.

8. The orthopedic device of claim 1 wherein the dual gears are bevel driven gears and are part of a dual gear unit which further comprises an alternately driven bevel drive gear, wherein gears are each mounted via a freewheel on a driven shaft.

9. The orthopedic device of claim 1, wherein the generator is coupled to a battery or capacitor.

10. The orthopedic device of claim 1, wherein the spring is a helical spring.

11. The orthopedic device of claim 1, wherein said component which consumes energy is an actuator or sensor.

* * * * *